(12) United States Patent
Fatone et al.

(10) Patent No.: US 10,813,675 B2
(45) Date of Patent: Oct. 27, 2020

(54) BONE FRACTURE FIXATION CLAMP WITH BONE REMODELING ADAPTABILITY

(71) Applicant: DePuy Synthes Products, Inc., Raynham, MA (US)

(72) Inventors: Peter Fatone, West Chester, PA (US); Dana Coombs, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/199,647

(22) Filed: Nov. 26, 2018

(65) Prior Publication Data

US 2019/0159819 A1 May 30, 2019

Related U.S. Application Data

(60) Provisional application No. 62/593,168, filed on Nov. 30, 2017.

(51) Int. Cl.
| | |
|---|---|
| *A61B 17/80* | (2006.01) |
| *A61B 17/86* | (2006.01) |
| *A61B 17/82* | (2006.01) |
| *A61B 17/68* | (2006.01) |
| *A61B 17/56* | (2006.01) |

(52) U.S. Cl.
CPC .......... *A61B 17/864* (2013.01); *A61B 17/68* (2013.01); *A61B 17/80* (2013.01); *A61B 17/809* (2013.01); *A61B 17/8019* (2013.01); *A61B 17/8023* (2013.01); *A61B 17/8061* (2013.01); *A61B 17/82* (2013.01); *A61B 2017/568* (2013.01); *A61B 2017/681* (2013.01); *A61B 2017/867* (2013.01)

(58) Field of Classification Search
CPC ............ A61B 17/7047; A61B 17/7056; A61B 17/7058–7059; A61B 17/80–808; B25B 5/067; B25B 5/082; B25B 5/101; B25B 5/125; F16L 33/06
USPC .................................................. 269/143, 249
See application file for complete search history.

(56) References Cited

U.S. PATENT DOCUMENTS

| | | | | |
|---|---|---|---|---|
| 1,156,440 | A | | 10/1915 | Smith |
| 2,460,470 | A | * | 2/1949 | Rogers ............... A61B 17/2812 606/86 R |
| 2,583,896 | A | * | 1/1952 | Siebrandt ............ A61B 17/808 606/86 R |
| 4,187,840 | A | * | 2/1980 | Watanabe ............ A61B 17/808 606/86 R |
| 7,666,210 | B2 | * | 2/2010 | Franck ............... A61B 17/7052 606/250 |

(Continued)

*Primary Examiner* — Eduardo C Robert
*Assistant Examiner* — Michelle C Eckman
(74) *Attorney, Agent, or Firm* — Fay Kaplun & Marcin, LLP

(57) ABSTRACT

A device for treating a bone includes a first clamp member sized and shaped to be mounted over a bone laterally across a fixation plate positioned along a length of the bone. In addition, the device includes a second clamp member coupleable to the first clamp member so that, when the first and second clamp members are coupled together in an operative position, the first and second clamp members extend about at least a portion of a periphery of the bone. The second clamp member includes a spring feature biased toward an initial configuration and deflectable toward a second configuration away from the bone.

15 Claims, 4 Drawing Sheets

(56) References Cited

U.S. PATENT DOCUMENTS

| | | | | |
|---|---|---|---|---|
| 8,231,623 B1* | 7/2012 | Jordan | A61B 17/64 | 606/250 |
| 8,579,950 B1* | 11/2013 | Jordan | A61B 17/8866 | 606/324 |
| 8,685,037 B1* | 4/2014 | Jordan | A61B 17/8866 | 606/105 |
| 8,784,450 B2* | 7/2014 | Moskowitz | A61B 17/0642 | 606/247 |
| 8,790,380 B2* | 7/2014 | Buttermann | A61B 17/707 | 606/324 |
| 9,113,961 B2* | 8/2015 | Larroque-Lahitette | A61B 17/7056 | |
| 9,775,650 B2* | 10/2017 | Buttermann | A61B 17/7032 | |
| 10,136,931 B1* | 11/2018 | Diao | A61B 17/8009 | |
| 2004/0087948 A1* | 5/2004 | Suddaby | A61B 17/7064 | 606/279 |
| 2005/0240187 A1* | 10/2005 | Huebner | A61B 17/80 | 606/71 |
| 2008/0009871 A1* | 1/2008 | Orbay | A61B 17/8866 | 606/70 |
| 2008/0103512 A1* | 5/2008 | Gately | A61B 17/7064 | 606/151 |
| 2009/0062869 A1* | 3/2009 | Claverie | A61B 90/50 | 606/324 |
| 2009/0163920 A1* | 6/2009 | Hochschuler | A61B 17/7064 | 606/74 |
| 2009/0270929 A1* | 10/2009 | Suddaby | A61B 17/1637 | 606/324 |
| 2010/0222793 A1* | 9/2010 | Skipper | A61B 5/6826 | 606/151 |
| 2011/0054547 A1* | 3/2011 | Anderson | A61B 17/0401 | 606/324 |
| 2011/0137353 A1* | 6/2011 | Buttermann | A61B 17/7001 | 606/305 |
| 2011/0144694 A1* | 6/2011 | Laeng | A61B 17/7037 | 606/263 |
| 2012/0290017 A1* | 11/2012 | Haidukewych | A61B 17/68 | 606/324 |
| 2012/0303068 A1* | 11/2012 | Fritzinger | A61B 17/808 | 606/286 |
| 2013/0090695 A1* | 4/2013 | Bernstein | A61B 17/808 | 606/281 |
| 2013/0131738 A1* | 5/2013 | Powell | A61B 17/68 | 606/324 |
| 2013/0261674 A1* | 10/2013 | Fritzinger | A61B 17/808 | 606/286 |
| 2015/0018888 A1* | 1/2015 | Geebelen | A61B 17/17 | 606/281 |
| 2015/0134009 A1* | 5/2015 | Licht | A61B 17/8076 | 606/281 |
| 2015/0209093 A1* | 7/2015 | Dallis | A61B 17/8023 | 606/281 |
| 2015/0289910 A1* | 10/2015 | Mirghasemi | A61B 17/8014 | 606/71 |
| 2016/0058478 A1* | 3/2016 | Agarwal | A61B 17/7032 | 606/270 |
| 2016/0066969 A1* | 3/2016 | Reuter | A61B 17/82 | 606/71 |
| 2016/0183981 A1* | 6/2016 | Schlaepfer | A61B 17/7055 | 606/324 |
| 2017/0014173 A1* | 1/2017 | Smith | A61B 17/1728 | |
| 2017/0172636 A1* | 6/2017 | Llas Vargas | A61B 17/823 | |
| 2017/0258508 A1* | 9/2017 | Katrana | A61B 17/282 | |
| 2018/0008321 A1* | 1/2018 | Stern | A61B 17/7002 | |
| 2018/0008330 A1* | 1/2018 | Taber | A61B 17/885 | |
| 2018/0098802 A1* | 4/2018 | Ananthan | A61B 17/8057 | |
| 2018/0132909 A1* | 5/2018 | Hackathorn, II | A61B 17/7065 | |
| 2018/0168707 A1* | 6/2018 | Shariati | A61B 17/8866 | |
| 2018/0193071 A1* | 7/2018 | Errico | A61B 17/8028 | |
| 2018/0263672 A1* | 9/2018 | Nelson | A61B 17/8061 | |
| 2019/0076154 A1* | 3/2019 | Herzog | A61B 17/15 | |
| 2019/0159819 A1* | 5/2019 | Fatone | A61B 17/864 | |
| 2019/0175235 A1* | 6/2019 | Kuroda | A61B 17/8004 | |

* cited by examiner

BONE FRACTURE FIXATION CLAMP WITH BONE REMODELING ADAPTABILITY

PRIORITY CLAIM

In present application claims priority to U.S. Provisional Patent Application Ser. No. 62/593,168 filed on Nov. 30, 2017; the entire disclosure is expressly incorporated herein by reference.

BACKGROUND

In some cases, fractures of long bones may be treated using bone fixation devices positioned on an outer surface of the bone. For example, the fixation of oblique fractures in long bones previously fitted with metal prostheses such as, for example, an intramedullary nail and/or a femoral stem, may preclude the use of bone fixation devices that extend into the bone if, for example, the previously inserted prosthesis would interfere with proper insertion of one or more of the fixation devices. Such bone fixation procedures therefore often use a combination of cables and metal compression plates employed with or without fixation screws that extend into the bone. After fixation, however, bone resorption may cause cables to lose their effectiveness.

SUMMARY OF THE INVENTION

The present embodiments are directed to a device for treating a bone, comprising a first clamp member sized and shaped to be mounted over a bone laterally across a fixation plate positioned along a length of the bone and a second clamp member coupleable to the first clamp member so that, when the first and second clamp members are coupled together in an operative position, the first and second clamp members extend about at least a portion of a periphery of the bone, the second clamp member including a spring feature biased toward an initial configuration and deflectable toward a second configuration away from the bone.

The present embodiments are also directed to a system for treating a bone, comprising a bone fixation plate configured to be positioned along a length of a bone, the bone fixation plate extending longitudinally from a first end to a second end and including a plurality of bone fixation element receiving openings extending therethrough and a fixation clamp including a first clamp member and a second clamp member coupleable to one another to extend about at least a portion of a periphery of the hone in an operative position, the first clamp member configured to be mounted over the bone fixation plate and the second clamp member being biased toward an initial configuration and deflectable toward a second configuration away from the bone.

The present embodiments are also directed to a method for treating a bone, comprising positioning a bone fixation plate along a length of a bone, assembling a first clamp member and a second clamp member of a fixation clamp about a portion of at least a portion of a periphery of the bone such that a first clamp member is mounted over the bone fixation plate to extend laterally thereacross, and tightening a coupling element fixing the first and second clamp members relative to one another such that a portion of the second clamp member deflects from an initial biased configuration toward a second configuration, the fixation clamp maintaining a radial compression about the bone as the second clamp member reverts toward the biased configuration as a cross-sectional area of the bone is reduced during healing of the bone.

BRIEF DESCRIPTION

DETAILED DESCRIPTION

Figure 1:
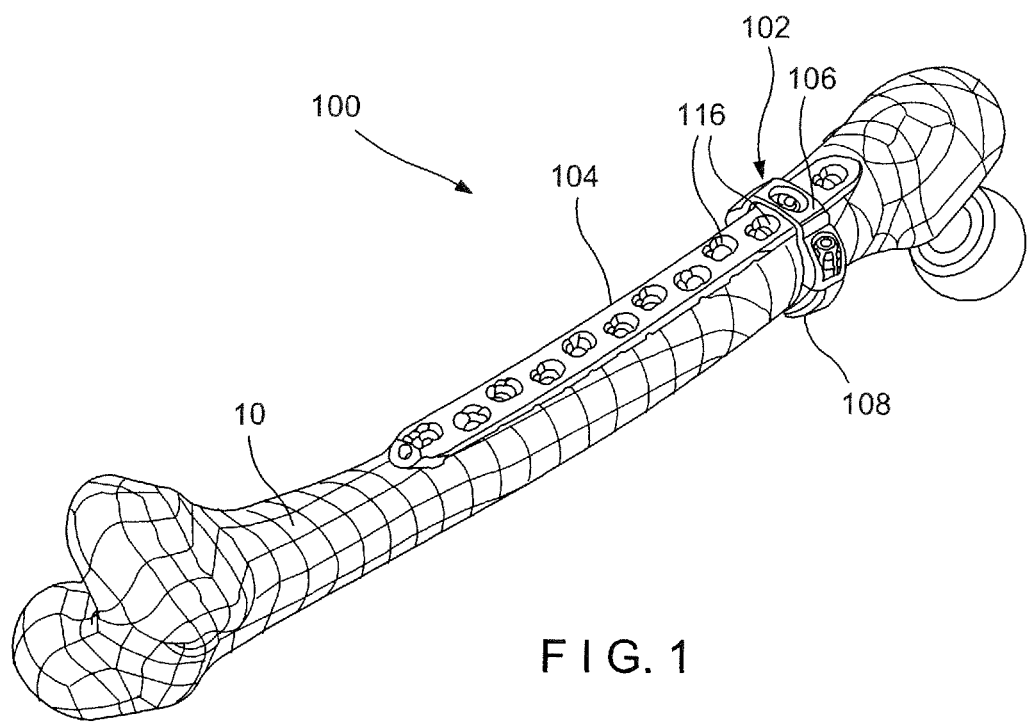
FIG. 1 shows a perspective view of a system for treating a bone according to an exemplary embodiment of the present disclosure.

The present embodiments may be understood with reference to the following description and the appended drawings, wherein like elements are referred to with the same reference numerals. The present embodiments relate to the treatment of bone fractures and, in particular, relate to the treatment of long bone diaphysis fractures. Exemplary embodiments describe a clamp which may be used in combination with a fixation plate where the clamp is configured to be clamped over the fixation plate and the bone to hold the fixation plate in an operative position at a target location on the bone. The clamp includes a spring feature which applies radial compression to the bone, even if bone resorption reduces a cross-sectional dimension of the bone. The clamp of the exemplary embodiment may be particularly useful for cases in which the long bone has been previously treated with a metal prosthesis which inhibits the use of fixation elements (e.g., fixation screws) through a portion thereof. It will be understood by those of skill in the art, however, that the clamp may also be utilized with other fixation elements, such as screws.

As shown in FIGS. 1-6, a system 100 for treating a fracture of a long bone according to an exemplary embodiment of the present disclosure comprises a fixation clamp 102 configured to be clamped about a bone 10 (e.g., femur) and a fixation plate 104 positioned along a length of the bone 10. The clamp 102 includes a first member 106 and a second member 108 configured to be coupled together to extend laterally across the fixation plate 104 and around a at least a portion of an outer periphery of the bone 10 to hold the fixation plate 104 in a desired position along the bone 10. In particular, the first member 106 is sized and shaped to be mounted over the fixation plate 104 while the second member 108 includes a spring feature 112 which permits deformation of the second member 108. That is, the clamp 102 is configured and sized so that, when the first member 106 and the second member 108 are coupled together and at rest, a circumference of an inner space formed by the clamp 102 (within which the bone 10 will be received) is smaller than a profile of a portion of bone (including the plate 104) over which the clamp is to be mounted or that this space may be reduced in size as described below so that the second member 108 is deflected radially outward to apply compression. Thus, when the clamp 102 is mounted over the target portion of bone, the second member 108 will be deflected radially outward away from this rest position so that the spring characteristics of the second member 108 apply compression to the bone 10. Thus, the first and second members 106, 108 are coupled together and mounted over the fixation plate 104 and at least partially circumferentially around the bone 10 deflecting the second member 108 radially outward to apply radial compression to the bone 10. If a cross-sectional area of the hone 10 decreases, for example, due to healing processes, the spring feature 112 continues to urge the second member 108 radially inward under its natural bias so that the clamp 102 maintains a desired level of radial compression about the bone 10 despite the decrease in size of the underlying portion of bone.

Each of the first and second members 106, 108 of the fixation clamp 102 of this embodiment has a substantially arcuate shape so that, when the first and second members 106, 108 are coupled together, a shape of the assembled fixation clamp 102 corresponds to a target portion of bone over which it is to be clamped (e.g., the diaphysis of the bone 10). The first member 106 of this embodiment extends arcuately from a first end 142 to a second end 146. The first member 106 is additionally sized and shaped to be mounted over a portion of the fixation plate 104 so that the first member 106 extends laterally across the fixation plate 104. In one embodiment, the first member 106 includes a groove 110 sized and shaped to receive the fixation plate 104 therein. The first member 106 may also include an opening 114 extending through a portion of the first member 106 including the groove 114 so that the first member 106 may be mounted over the fixation plate 104 with the opening 114 in alignment with a bone fixation element receiving opening 116 of the fixation plate 104. In other words, once the first member 106 has been mounted over the fixation plate 104 and assembled with the second member 108 of the fixation clamp 102 to at least partially encircle the bone 10, a bone fixation element may be inserted through the opening 114 of the first member 106 and the opening 116 of the fixation plate 104 with which it is aligned, to provide further fixation of the fixation clamp 102 to the bone 10.

The first member 106 may also include a channel 118 extending through the first end 142, the channel 118 configured to receive a stem portion 122 of the second member 108 slidably therein to couple the first and second members 106, 108, as will be described in further detail below. The channel 118 extends from a first opening 146 at the first end 142 to a second opening 148 proximate the groove 110. The channel 118 extends through the first member 106 so that, when the first member 106 is mounted over the fixation plate 104, the channel 118 extends along a side of the bone 10, laterally of the fixation plate 104. In other words, an axis along which the channel 118 extends, extends laterally relative to a portion of the first member 106 including the groove 110. Thus, the channel 118 does not interfere with the groove or the fixation plate 104 received therein, allowing assembly of first and second members 106, 108 so that the fixation clamp 102 at least partially encircles the bone 10.

Proximate the second end 144, the first member 106 of this embodiment includes another opening 120 extending through a portion of the first member 106 between the groove 110 and the second end 144 so as not to interfere with the mounting of the first member 106 over the fixation plate 104. The opening 120 is configured to receive a bone fixation element therethrough so that, if so desired, a bone fixation element may be inserted therein and into the bone 10 to provide further fixation of the clamp 102 to the bone 10.

Figure 2:
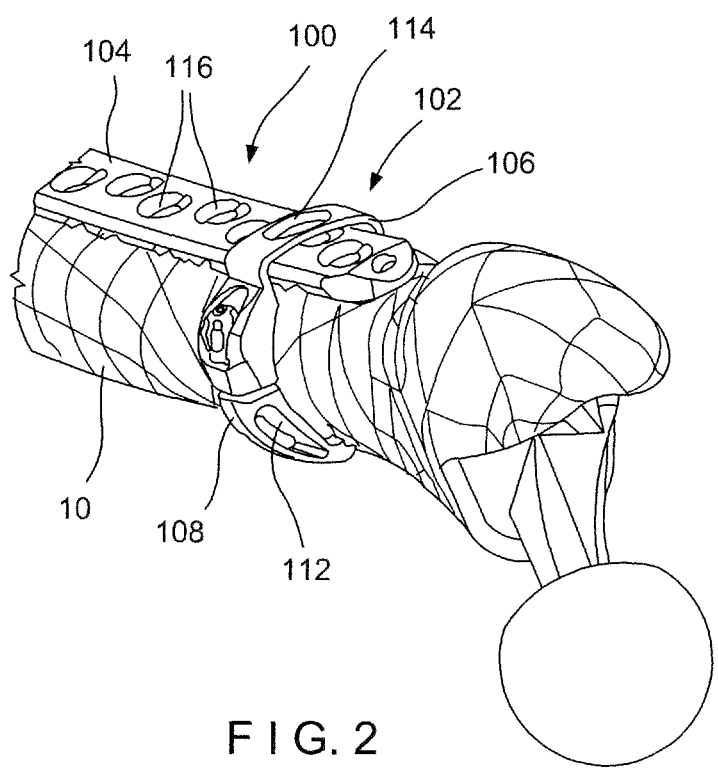
FIG. 2 shows an enlarged perspective view of a portion of the system of FIG. 1.
Figure 3:
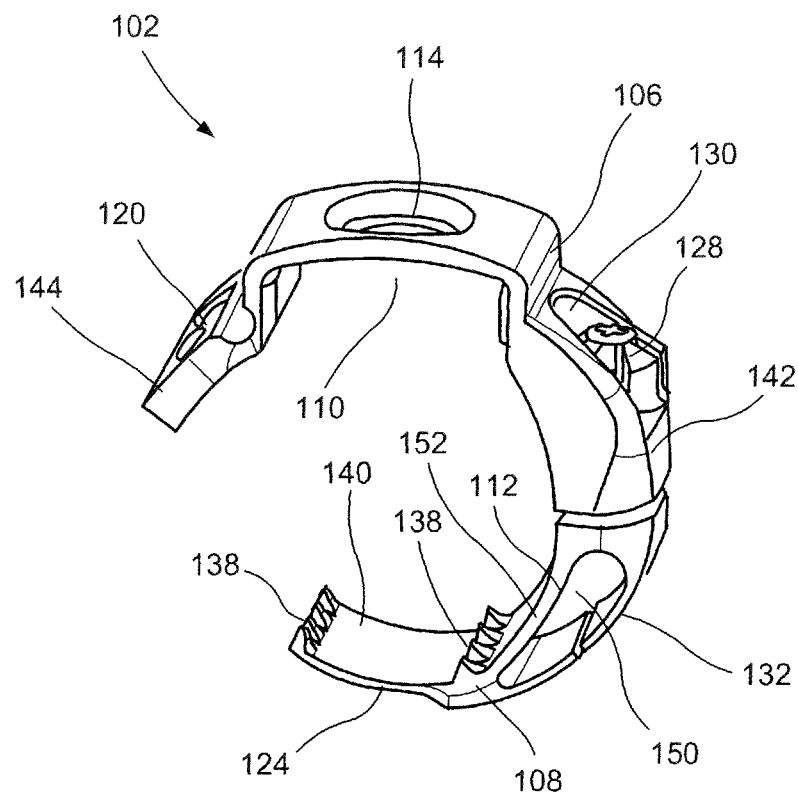
FIG. 3 shows a perspective view of a fixation clamp according to the system of FIG. 1.
Figure 4:
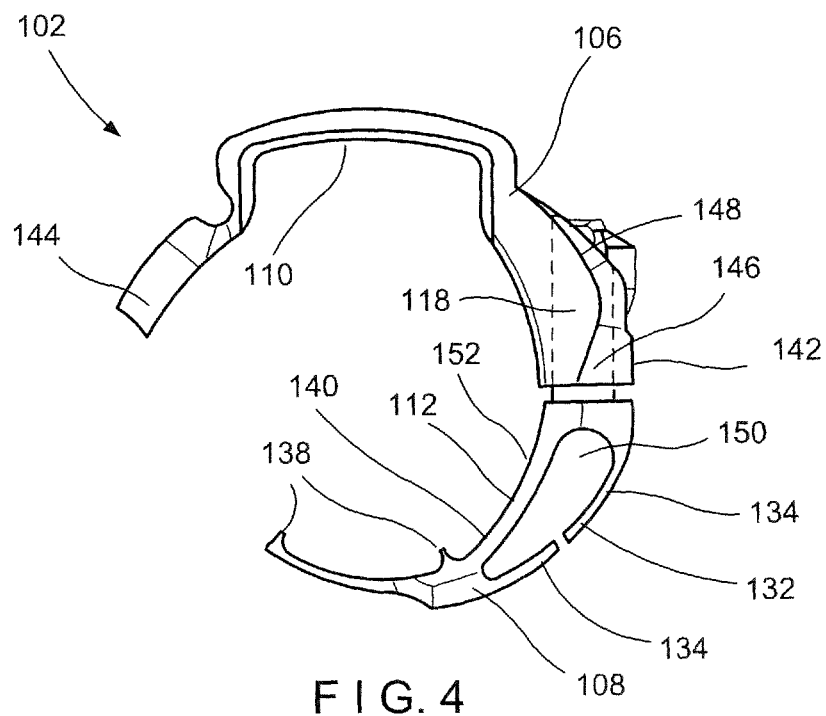
FIG. 4 shows a side view of a fixation clamp according to the system of FIG. 1.
Figure 5:
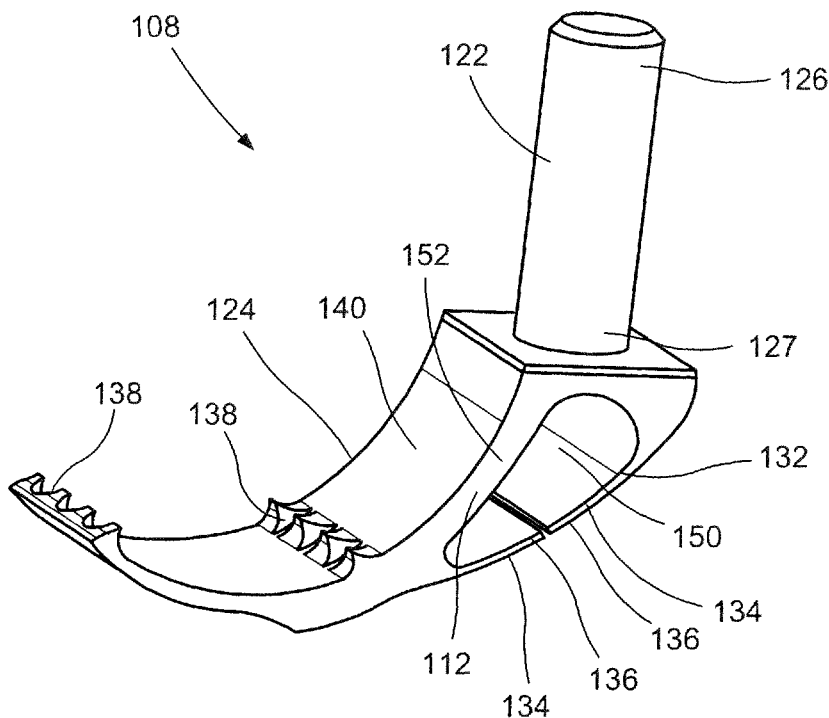
FIG. 5 shows a perspective view of a second clamp member of the fixation clamp according to the system of FIG. 1.
Figure 6:
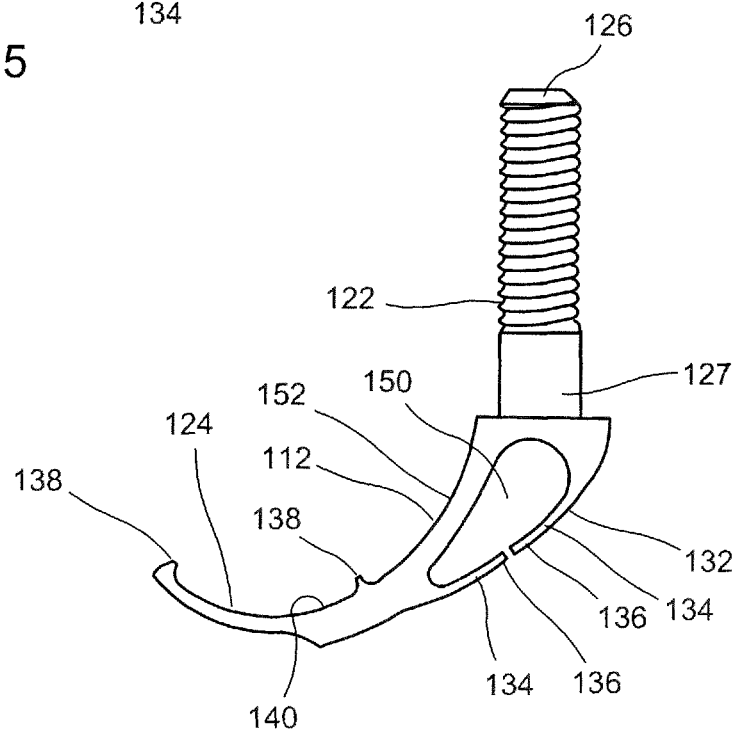
FIG. 6 shows a side view of the second clamp member according to the system of FIG. 1.

In one embodiment, the second member 108 includes the stem portion 122, for coupling the first and second members 106, 108 together, and an arcuate portion 124 extending therefrom so that, when the first and second members 106, 108 are coupled together, the assembled fixation clamp 102 at least partially encircles the bone 10 over which it is clamped. The stem portion 122 extends longitudinally from a first end 126 to a second end 127 and is sized and shaped to be slid longitudinally into the channel 118 of the first member 106. The stem portion 122 extends along a substantially straight path and a length of the stein portion 122 is selected so that, when the stem portion 122 is inserted through the first opening 146 of the channel 118, the first end 126 of the stem portion 122 extends beyond the second end 148 of the channel 118. The stem portion 122 may include a threading along a portion thereof so that, when the stem portion 122 is inserted through the channel 118, a coupling element 128 such as, for example, a nut, may be threaded over the end 126 extending beyond the end of the channel 118 to couple the first and second member 106, 108 together, at a desired position and configuration relative to one another. As shown in FIGS. 1-2, the coupling element 128 may be seated within a recess 130 of the first member 106 so as not to protrude substantially beyond an outer profile of the first member 106 when the first and second member 106, 108 are coupled together to form the assembled fixation clamp 102.

The arcuate portion 124 extends from the second end 127 of the stem portion 122 so that, when the second member 108 is coupled to the first member 106 and placed in a desired operative position, the arcuate portion 124 extends about at least a portion of a periphery of the bone 10. The arcuate portion 124 is formed to include the spring feature 112 biasing the arcuate portion 124 toward a first configuration from which the arcuate portion 124 is deflected radially outward (toward a second configuration so that it may be positioned about a target portion of bone) without plastic deformation of the arcuate portion 124. The spring feature 112 may be configured as, for example, a leaf spring preloaded to apply a known radially compressive force for known radially outward displacement as would be understood by those skilled in the art. In other words, this preload allows the assembled fixation clamp 102 to maintain compression on the bone 10 even if the dimensions of the bone are reduced (e.g., due to bone resorption) so long as the bone dimensions are reduced within the amount by which the arcuate portion 124 is initially displaced radially outward from its resting position (i.e., distance that the arcuate portion 124 is flexed away from the first member 106 when initially placed on the target portion of bone).

Figure 7:
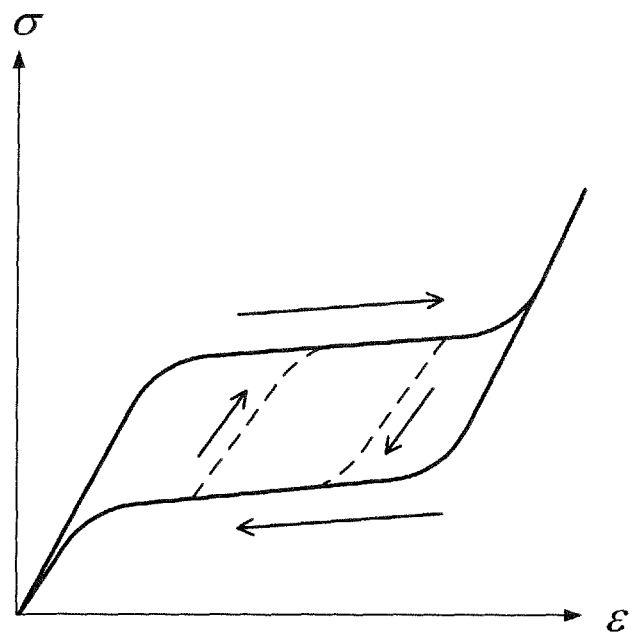
FIG. 7 shows a table of a pseudoelastic Nitinol phase demonstrating a full loading path (shown in sold lines) and a partial loading path (shown in dashed lines)

In one exemplary embodiment, at least a portion of the arcuate portion 124 including the spring feature 112 is formed of a material such as, for example, Nitinol, which permits distortion of the arcuate portion 124 within a desired range without plastic deformation. The super elastic behavior of Nitinol allows it to undergo large elastic deformations, approaching 8-10% strain, and have stiffness greater than similarly flexible materials without permanent plastic deformation. As shown in the stress strain curve of FIG. 7, the stress, and therefore the load, will remain almost constant in the plateau region of the curve. This allows a large displacement of the arcuate portion 124 with a nearly constant compressive load applied to the bone 10, which permits for full recovery with no permanent deformation of the arcuate portion 124 as the bone segment settle. It will be understood by those of skill in the art, however, that the arcuate portion 124 may be formed of any of a variety of materials, however, so long as the arcuate portion 124 is permitted to flex/deform as described above. For example, the arcuate portion 124 may also be formed of 316 stainless steel, a titanium alloy and/or pure titanium.

The arcuate portion 124 may also be formed to include a stop feature 132 which prevents the arcuate portion 124 from being deflected beyond a maximum permitted displacement. In other words, the stop feature 132 defines a range of permitted deflection of the arcuate portion 124. In one example, the stop feature 132 may be defined via a pair of wings 134 which extend toward one another along an exterior of the arcuate portion 124—i.e., a portion of the arcuate portion facing away from the bone 10 in the operative position. Tips 136 of the wings are separated from one another by a distance corresponding to the desired maximum displacement so that, when the arcuate portion 124 is deflected, the tips 136 are moved toward one another. Once the tips 136 come into contact with one another, the arcuate portion 124 is prevented from deflecting any further. The tips 136 may include a beveled edge to prevent stress upon contact between the two tips 136. In one embodiment, the tips 136 may be separated from one another by a distance ranging from between 0.2 mm-1.0 mm. In one particular embodiment in which the arcuate portion 124 is formed via a titanium alloy, the distance between the tips 136 may be approximately 0.4 mm. It will be understood by those of skill in the art, however, that the distance between the tips 136 may vary depending on a material and/or a thickness of the arcuate portion 152.

In one embodiment, the spring feature 112 and the stop feature 132 may be defined via a slot 150 extending through the arcuate portion 124. The slot 150 extends substantially parallel to a longitudinal axis of the bone 10, when the clamp 102 is in the operative position. The slot 150 is sized and shaped so that the spring feature 112 resulting therefrom is a reduced thickness portion 152 of the arcuate portion 124 which allows deflection of the arcuate portion 124 therealong. The slot 150 defines the wings 134 of the stop feature 132 and is open to an exterior of the clamp 102 via the distance between the tips 136 of the wings 134.

The arcuate portion 124 also includes teeth 138 extending from an interior surface 140 (e.g., a surface facing toward the bone 10 in the operative position) thereof for engaging and/or gripping a bone 10 about which the fixation clamp 102 is fixed. Although the exemplary embodiments specifically show and describe the arcuate portion 124 as including teeth 138, it will be understood by those of skill in the art that the arcuate portion 124 may include other projections and/or surface features for facilitating a gripping of the bone 10.

According to an exemplary method using the system 100, the fixation plate 104 is placed in a desired position along the bone 10. To provide fixation of the plate 104 to the bone 10, the first member 106 may be mounted over a portion of the fixation plate 104 and assembled with the second member 108 by inserting the stem portion 122 of the second member 108 into the channel 118 of the first member 106. The stem portion 122 is inserted through the channel 118 until the first end 126 of the stem portion 122 extends beyond the second end 148 of the channel 118. The coupling element 128 may then be threaded over the first end 126 to couple the first and second members 106, 108 to one another. The coupling element 128 is threaded over the stem portion 126, drawing the second member 108 toward the first member 106, until the spring feature 112 of the arcuate portion 124 causes a deflection of the arcuate portion 124. The arcuate portion 124 may be deflected until the tips 136 of the wings 34 of the stop feature 132, contact one another, preventing further deflection of the arcuate portion 124.

The clamp 102 may be assembled over the fixation plate 104 so that the opening 114 is aligned with a bone fixation element receiving opening 116 of the fixation plate 104 so that a bone fixation element (e.g., bone screw) may be inserted through the openings 114, 116 to provide further fixation of the clamp 102 and the plate 104 to the bone 10. A bone fixation element may also be inserted through the opening 120 to provide additional fixation of the clamp 102 to the bone 10.

As described above, the spring feature 112 of the arcuate portion 124 permits the clamp 102 to provide continuous compression of the bone 10, even as bone resorption occurs and the bone settles, resulting in reduced dimensions of the bone 10. As described above, the clamp 102 may be particularly useful for cases in which a previous prosthetic has been inserted through a portion of the bone 10. For example, the clamp 102 may be useful for fixing bones in which an intramedullary nail or a femoral stem has already been implanted into the bone. Thus, in one embodiment, as shown in FIGS. 1 and 2, the clamp 102 may be fixed about a proximal portion of a femur in which a femoral stem has been previously implanted. It will be understood by those of skill in the art, however, that the clamp 102 may be used to fix a fixation plate 104 to any long bone, along any portion thereof. It will also be understood by those of skill in the art that multiple clamps 102 may be used to fix the fixation plate 104 to the bone 10. Additionally, fixation screws may be inserted through any of the bone fixation element receiving openings 116 of the fixation plate 104 to provide additional fixation of the plate 104 to the bone 10 to the extent this is possible without interference from the femoral stem.

Although the exemplary embodiment shows and describes coupling of the first and second members 106, 108 via the stem portion 122 and the coupling element 128, it will be understood by those of skill in the art that the first and second members 106, 108 may be coupled to one another in any of a variety of ways so long as the first and second members 106, 108 may be coupled to at least partially encircle the bone 10 and provide radial compression thereto. For example, in another embodiment, the first and second members 106, 108 may be coupled to one another via a bolt inserted through the channel 118 and a corresponding channel of the second member 108. The bolt may threadedly engage the second member 108 so that rotation of the bolt causes the first and second members to be moved toward one another until the arcuate portion 124 deflects, as desired.

Figure 8:
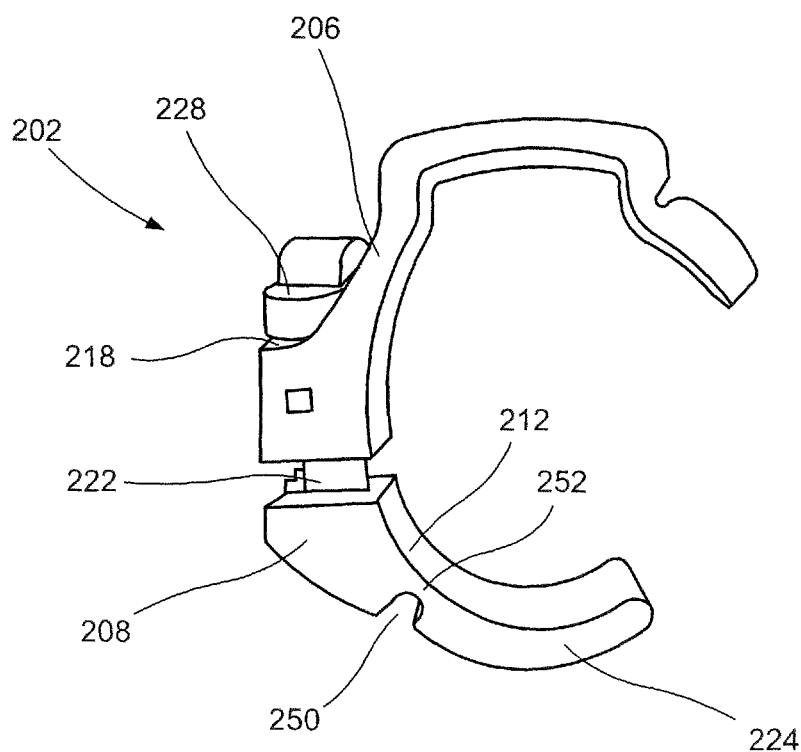
FIG. 8 shows a side view of a fixation clamp according to another exemplary embodiment of the present invention.

As shown in FIG. 8, a fixation clamp 202 according to another exemplary embodiment of the present invention may be substantially similar to the fixation clamp 102 for clamping about a bone and a fixation plate substantially similar to the fixation plate 104 described above with respect to the system 100. Similarly to the fixation clamp 102, the fixation clamp 202 comprises a first member 206 and a second member 208 which may be coupled together to extend laterally across the fixation plate and about at least a portion of an outer periphery of the bone to hold the fixation plate in a desired position along the bone. The first member 206 is sized and shaped to be mounted over the fixation plate, while the second member 208 includes a spring feature 212 which permits deformation of the second member 208 so that the fixation clamp 202 may apply a continuous radial compression about the bone even when the cross-sectional area of the bone is reduced, as described above with respect to the system 100. The first and second members 206, 208 may be substantially similar to the first and second members 106, 108, respectively, of the fixation clamp 102.

Rather than a spring feature including a slot defining a reduced thickness portion and a stop feature including a pair of wings, the spring feature 212 of the fixation clamp 202 includes a groove 250 formed along an exterior surface (e.g., a surface facing away from the bone in the operative position) of an arcuate portion 224 of the second member 208. The groove 250 defines a point 252 having a reduced thickness about which the arcuate portion 224 is deflectable. The groove 250 also acts to define a maximum possible deflection of the arcuate portion 224.

The first and second members 206, 208 are coupleable to one another in any of a variety of ways and, in one particular embodiment, may be coupled via a channel 218 extending through the first member 206 and a stem portion 222 of the second member 208 fixed via a coupling element 228, as described above with respect to the fixation clamp 102. The first and second members 206, 208 are coupled about the bone until the arcuate portion 224 deforms. As the bone heals and a cross-sectional area of the bone is reduced, the arcuate portion 224 reverts toward its initial biased configuration, providing a continued radial compression on the bone.

Although the exemplary embodiments specifically show and describe the spring feature of the second member as including a groove and/or slot to define a reduced thickness portions to permit deflection of the second member, it will be understood by those of skill in the art that the spring feature of the second member may be achieved in any of a variety of ways. For example, the elastic properties of the material of the arcuate portion of the second clamp member may be sufficient to permit deflection of the second member.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A device for treating a bone, comprising:
   a first clamp member sized and shaped to be mounted over a bone laterally across a fixation plate positioned along a length of the bone, wherein the first clamp member includes a channel extending therethrough from a first opening at an end of the first clamp to a second opening; and
   a second clamp member coupleable to the first clamp member so that, when the first and second clamp members are coupled together in an operative position, the first and second clamp members extend about at least a portion of a periphery of the bone, the second clamp member including a spring feature biased toward an initial configuration, the initial configuration being arranged so that, as the spring feature is deflected away from the initial configuration, the spring feature applies radial compression against the bone, the second clamp member including a stem portion sized and shaped be slidably inserted through the first opening of the channel so that an end of the stem portion extends beyond the second opening.

2. The device of claim 1, wherein at least a portion of the second clamp member is formed of Nitinol.

3. The device of claim 1, wherein the first clamp includes a groove sized and shaped to receive a fixation plate therein.

4. The device of claim 1, further comprising a coupling element configured to threadedly engage the end of the stem portion to fix the first and second clamp members relative to one another.

5. The device of claim 1, wherein the spring feature is defined by a reduced thickness portion of the second clamp member.

6. The device of claim 5, wherein the reduced thickness is defined via a groove extending into an exterior surface of the second clamp member.

7. The device of claim 1, further comprising a stop feature defining a maximum possible deflection of the second clamp member.

8. The device of claim 7, wherein the stop feature is defined via a pair of wings extending along an exterior surface of the second clamp member, tips of the pair of wings extending toward one another and separated from one another by a distance corresponding to the maximum possible deflection of the second clamp member.

9. The device of claim 1, wherein an interior bone-facing surface of the second clamp member includes teeth for gripping a bone over which the fixation clamp is fixed.

10. The device of claim 1, a portion of the first clamp including a hole extending therethrough for receiving a bone fixation element therein.

11. A system for treating a bone, comprising:
    a bone fixation plate configured to be positioned along a length of a bone, the bone fixation plate extending longitudinally from a first end to a second end and including a plurality of bone fixation element receiving openings extending therethrough; and
    a fixation clamp including a first clamp member and a second clamp member coupleable to one another to extend about at least a portion of a periphery of the bone in an operative position, the first clamp member configured to be mounted over the bone fixation plate and the second clamp member being biased toward an initial configuration, the initial configuration being arranged so that, as the spring feature is deflected away from the initial configuration, the spring feature applies radial compression against the bone, wherein the first clamp member includes a channel extending therethrough from a first opening at an end of the first clamp to a second opening and the second clamp member includes a stem portion sized and shaped be slidably inserted through the first opening of the channel so that an end of the stem portion extends beyond the second opening.

12. The system of claim 11, wherein at least a portion of the second clamp member is formed of Nitinol.

13. The system of claim 11, wherein the first clamp includes a groove sized and shaped to receive a fixation plate therein.

14. The system of claim 11, wherein the second clamp member includes a reduced thickness portion defining a deflectable portion of the second clamp member.

15. The system of claim 11, wherein the fixation clamp includes a stop feature defining a maximum possible deflection of the second clamp member.

* * * * *